US008078281B2

(12) United States Patent
Priori et al.

(10) Patent No.: US 8,078,281 B2
(45) Date of Patent: Dec. 13, 2011

(54) APPARATUS FOR TREATING NEUROLOGICAL DISORDERS BY MEANS OF CHRONIC ADAPTIVE BRAIN STIMULATION AS A FUNCTION OF LOCAL BIOPOTENTIALS

(75) Inventors: Alberto Priori, Virgilio (IT); Guglielmo Foffani, Milan (IT); Lorenzo Rossi, Trento (IT)

(73) Assignees: Fondazione IRCCS "CA' Granda - Ospedale Maggiore Policlinico", Milan (IT); Universita' Degli Studi di Milan, Milan (IT)

( * ) Notice: Subject to any disclaimer, the term of this patent is extended or adjusted under 35 U.S.C. 154(b) by 898 days.

(21) Appl. No.: 12/091,313

(22) PCT Filed: Aug. 3, 2006

(86) PCT No.: PCT/IB2006/002184
§ 371 (c)(1),
(2), (4) Date: Apr. 24, 2008

(87) PCT Pub. No.: WO2007/049105
PCT Pub. Date: May 3, 2007

(65) Prior Publication Data
US 2008/0269836 A1    Oct. 30, 2008

(30) Foreign Application Priority Data

Oct. 28, 2005   (IT) .............................. MI2005A2061

(51) Int. Cl.
*A61B 5/04*   (2006.01)
(52) U.S. Cl. ........................................................ 607/45
(58) Field of Classification Search ..................... 607/45
See application file for complete search history.

(56) References Cited

U.S. PATENT DOCUMENTS 5,683,422 A    11/1997  Rise
(Continued)

FOREIGN PATENT DOCUMENTS
WO    WO0007494 A2    2/2002

OTHER PUBLICATIONS

Brown, et al., "Basal Ganglia Local Field Potential Activity: Character and Functional Significance in the Human", Clinical Neurophysiology, No. 116, 2005, pp. 2510-2519.

(Continued)

*Primary Examiner* — Eric D Bertram
(74) *Attorney, Agent, or Firm* — Pearne & Gordon LLP

(57) ABSTRACT

An apparatus and a related method for the deep brain stimulation have been invented wherein the parameters of the stimulation supplied at the human nervous system level are adjusted and optimized continuously by the analysis of the bioelectric signals coming from the tissue adjacent the stimulation electrode itself, adapting the therapy continuously and in line to the patient's clinical state. The apparatus is constituted at least by an electro-catheter (1) implantable in a patient's brain and equipped with four contacts (4, 5, 6, 7). Then, there is at least a stimulation module (9) which generates the stimulating signal (15) sent to the electro-catheter (1) and in particular to one of the contacts thereof (6). The electro-catheter (1) contemporarily sends a signal characterizing the brain activity coming from the tissue involved by the stimulating signal (15) to an acquisition module (8). The characterizing signal is used to determine the feedback of the stimulation parameters (15) and, consequently, to adapt the therapy continuously to the patient's clinical state.

11 Claims, 5 Drawing Sheets

U.S. PATENT DOCUMENTS

| | | | |
|---|---|---|---|
| 6,366,813 | B1 | 4/2002 | DiLorenzo |
| 6,480,743 | B1 | 11/2002 | Kirkpatrick et al. |
| 2001/0029391 | A1 | 10/2001 | Gluckman et al. |
| 2002/0177882 | A1 | 11/2002 | DiLorenzo |
| 2003/0114886 | A1* | 6/2003 | Gluckman et al. ............... 607/2 |
| 2004/0073273 | A1 | 4/2004 | Gluckman et al. |
| 2005/0065427 | A1 | 3/2005 | Magill et al. |

OTHER PUBLICATIONS

Kuhn, et al., "The Relationship Between Local Field Potential and Neuronal Discharge in the Subthalamic Nucleus of Patients With Parkinson's Disease", Experimental Neurology, 2005, pp. 212-220, No. 194, Elsevier Ireland.

Levy, et al., "Dependence of Subthalamic Nucleus Oscillations on Movement and Dopamine in Parkinson's Disease", Brain, 2002, pp. 1196-1209, Guarantors of Brain.

Priori, et al., "Rhythm-Specific Pharmacological Modulation of Subthalamic Activity in Parkinson's Disease", Experimental Neurology, 2004, pp. 369-379, No. 189, Elsevier Inc.

Brown, et al., "Dopamine Dependency of Oscillations Between Subthalamic Nucleus and Palladium in Parkinson's Disease", J. Neurosci, Feb. 2001, pp. 1033-1038, Abstract.

Brown, "Oscillatory Nature of Human Basal Ganglia Activity; Relationship to the Pathophysiology of Parkinson's Disease", Mov. Disord., Apr. 2003, pp. 357-363, Abstract.

Priori, et al, "Movement-Related Modulation of Neural Activity in Human Basal Ganglia and its L-Dopa Dependency: Recordings From Deep Brain Stimulation Electrodes in Patients With Parkinson's Disease", Neurol. Sci., Sep. 2002, pp. S101-S102, Abstract.

Cassidy, et al., "Movement-Related Changes in Synchronization in the Human Basal Ganglia", Brain, Jun. 2002, pp. 1235-1246, Abstract.

Doyle, et al., "Levodopa-Induced Modulation of Subthalamic Beta Oscillations During Self-Paced Movements in Patients With Parkinson's Disease", Eur. J. Neurosci., Mar. 2005, pp. 1403-1412, Abstract.

Foffani, et al., "300-HZ Subthalamic Oscillations in Parkinson's Disease", Brain, Oct. 2003, pp. 2153-2163, Abstract.

Foffani, et al., "Adaptive Autoregressive Identification With Spectral Power Decomposition for Studying Movement-Related Activity in Scalp EEG Signals and Basal Ganglia Local Field Potentials", J. Neural Eng., Sep. 2004, pp. 165-173, Abstract.

Foffani, et al, "Physiological Recordings From Electrodes Implanted in the Basal Ganglia for Deep Brain Stimulation in Parkinson's Disease, The Relevance of Fast Subthalamic Rhythms", Acta Neurochir. Suppl., 2005, pp. 97-99, Abstract.

Foffani, et al., "Altered Subthalamo-Pallidal Synchronisation in Parkinsonian Dyskinesias", J. Neural Neurosurg. Psychiatry, Mar. 2005, pp. 426-428, Abstract.

Foffani, et al, "Movement-Related Frequency Modulation of Beta Oscillatory Activity in the Human Subthalamic Nucleus", J. Physiol., Oct. 2005, pp. 699-711, Abstract.

Fogelson, et al, "Reciprocal Interactions Between Oscillatory Activities of Different Frequencies in the Subthalamic Region of Patients With Parkinson's Disease", Eur. J. Neurosci., Jul. 2005, pp. 257-266, Abstract.

Kuhn, et al, "Event-Related Beta Desynchronization in Human Subthalamic Nucleus Correlates With Motor Performance", Brain, Apr. 2004, pp. 735-746, Abstract.

Williams, et al, "Dopamine-Dependent Changes in the Functional Connectivity Between Basal Ganglia and Cerebral Cortex in Humans", Brain, Jul. 2002, pp. 1558-1569, Abstract.

Silberstein, et al, "Patterning of Globus Pallidus Local Field Potentials Differs Between Parkinson's Disease and Dystonia", Brain, Dec. 2003, pp. 2597-2608, Abstract.

* cited by examiner

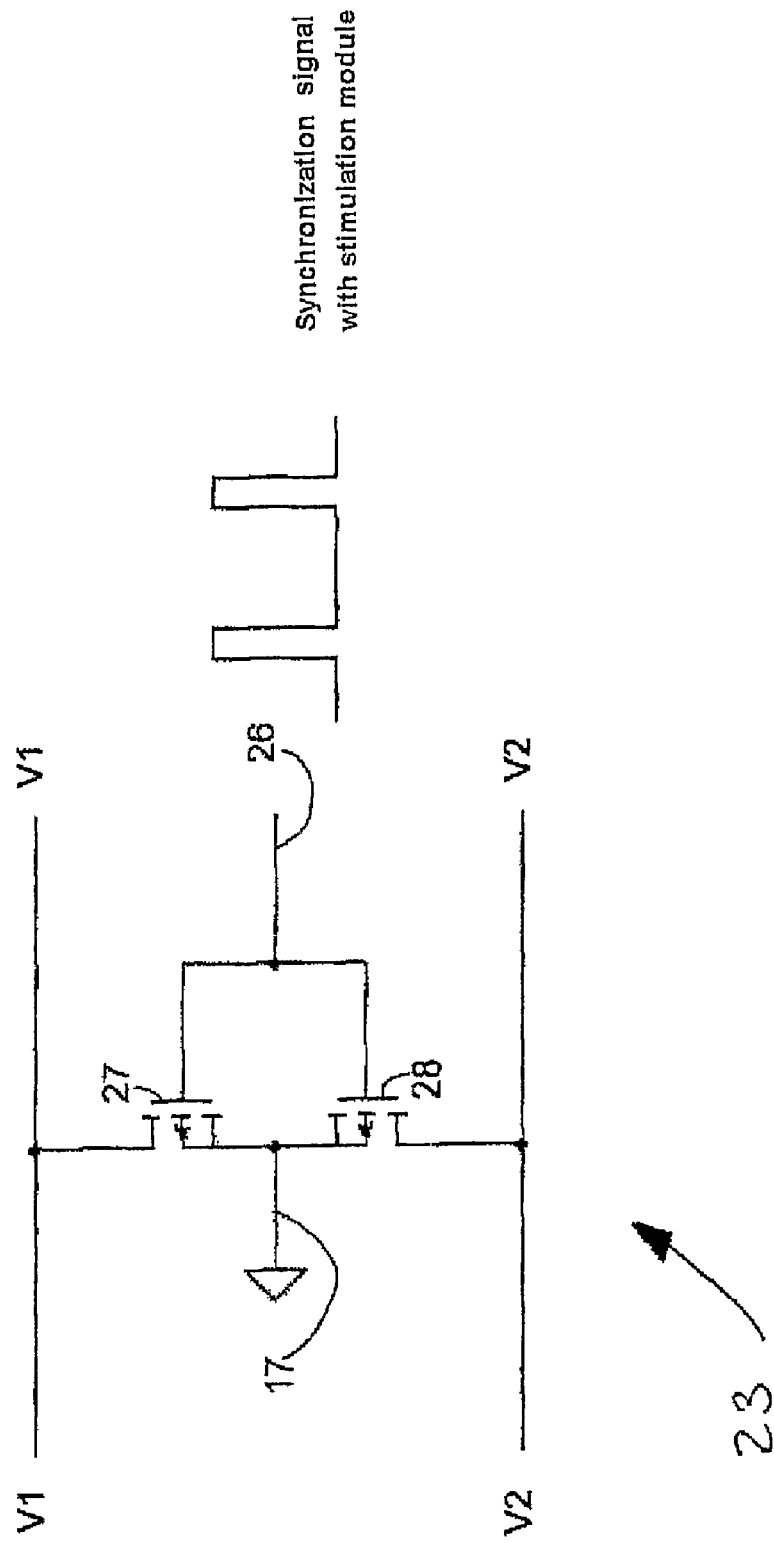

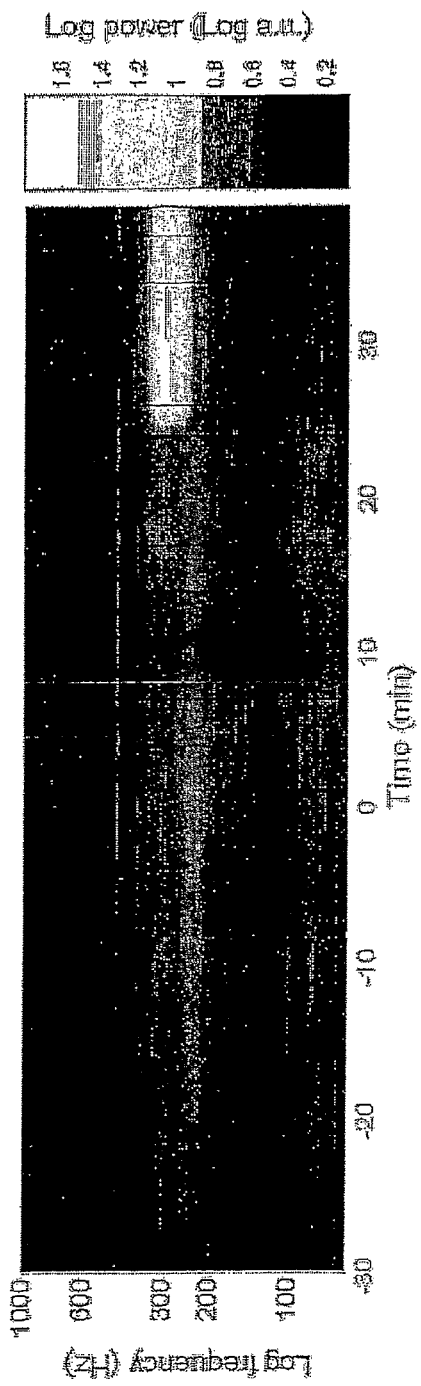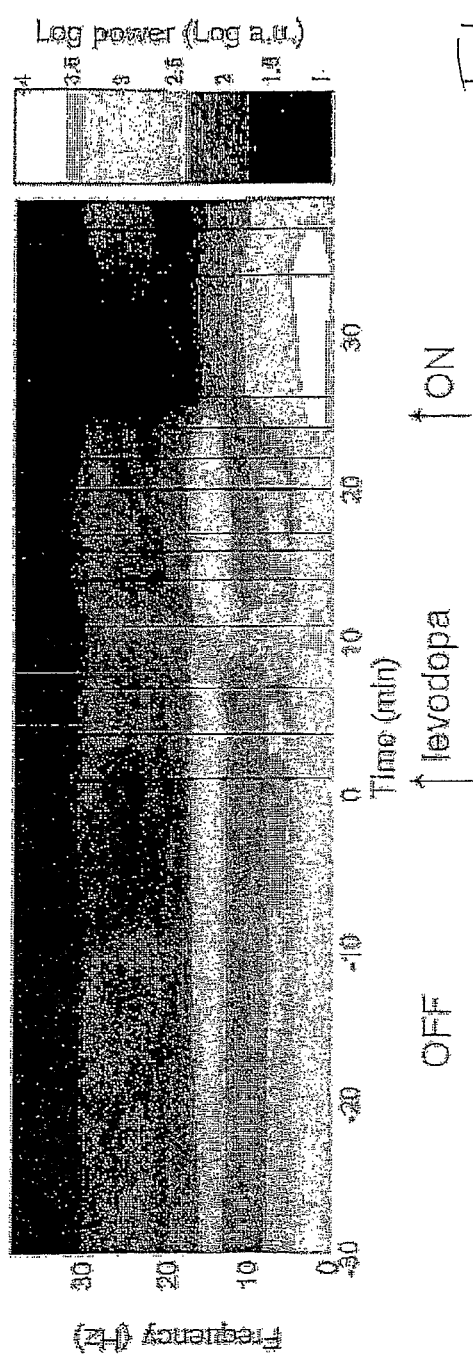
FIG. 6

APPARATUS FOR TREATING NEUROLOGICAL DISORDERS BY MEANS OF CHRONIC ADAPTIVE BRAIN STIMULATION AS A FUNCTION OF LOCAL BIOPOTENTIALS

The object of the present invention is an apparatus for treating neurological disorders by means of adaptive electro-stimulation.

The invention relates to a system of feedbacked deep brain stimulation which is able to detect biopotentials from the stimulating electrode or by adjacent electrodes, to correlate such signals to the stimulation effects and feedback the stimulus parameters in order to optimize the therapy. Under local biopotentials, the electrical potentials produced by groups of neurons proximate the recording and stimulation electrodes are meant. As it is known the Deep Brain Stimulation (or DBS) is a therapeutic method based upon the modulation of the activity of structures of the central nervous system by means of the chronic electric stimulation supplied locally. The electrodes are implanted for treating the disorders of movement, epilepsy, headache, some psychiatric and pain disorders, by means of a stereotactic neurosurgical procedure. The methodology allows improving the patients to the benefit of the functional autonomy and the life quality. Since currently the Parkinson Disease is the disorder therefor the methodology use is consolidated, the present invention will be mainly referred thereto. The surgical treatment of the Parkinson disease historically started with lesional ablative procedures such as the pallidotomy and the thalamotomy. With the arrival of L-Dopa pharmacological treatment during the '70s, one observed a progressive abandonment of the surgical therapy. It was then taken into account again around mid '80s, with the pioneer studies of Benabid and Pollack in Grenoble, who proposed the high-frequency brain stimulation methodology. The principle is that of functional inactivation of the target structure. At first DBS had as targets the thalamic nuclei for the treatment of the Essential Tremor, then it was also used in the inner globus pallidus and in the subthalamic nucleus for the dystonia and the Parkinson disease. The system implantation procedure is relatively sure, little invasive and, at least in the Parkinson disease, it is carried out under local anesthesia. Once detected the target structure, one proceeds with the stereotactic localization thereof with the procedures of pre-surgical identification mainly based upon the encephalon's computed tomography and magnetic resonance. Subsequently, one proceeds with the trapanation of the cranial theca by inserting into the brain parenchyma exploring electrodes for the intra-surgical monitoring which allow recording the cellular activity during the systems of adaptive stimulation feedback by physiological signals. The U.S. Pat. No. 6,480,743, in the name of Benjamin D. et al., describes an adaptive stimulation system, in case equipped with a single electro-catheter, which analyses the electro-encephalographic signals to detect the presence of epileptic crises and consequently it activates a brain stimulation apt to inhibit the epeleictogen focus before the clinical crisis. However, such methodology excludes the in-chronic stimulation, necessary for the Parkinson disease, not providing any system for the contemporary recording of local biopotentials from the stimulating electrodes or from contiguous electrodes. The U.S. Pat. No. 5,683,422, in the name of Rise, describes a deep brain stimulation system, currently utilized as definitive implantation for the Parkinson's disease, which in case is feedback by a signal generated by sensors in case integrated in the same stimulation electro-catheter. Such sensors measure the superexcitation of a subthalamus portion proximate the stimulation site. In the preferred configuration such superexcitation is measured through an electro-chemical sensor which generates an electric signal utilized for feedbacking the stimulation coupled to an analog-to-digital converter by means of two conductors. The method proposed by Rise differs substantially from what proposed hereinafter in that it is based upon the use of an electro-chemical/biochemical, and not bioelectric, signal. The limits of the Rise invention are given by the nature of the electro-chemical signals therefor, apart from the currently available partial information about the biochemical processes of the nervous tissue in relation to the phenomenology of the Parkinson's disease, there is a latency time, given by the current technologies and by the tissue physiology, between the alterations of the subject's pathologic state and the tissue biochemical variations which makes difficult a sufficiently quick feedback stimulation avoiding system oscillations. On the contrary, the use of local biopotentials, the features thereof correlated to subject's pathologic states are known more in details, involves a minimum latency between the modification of the patient's clinic conditions and the time wherein the variation of the local biopotentials can be detected. In order to measure such local biopotentials, a system for removing the artefact not mentioned in the Rise's claims is strictly necessary, therefore the present invention provides important innovation features to the method proposed by Rise. Additional features and advantages will be more evident from the detailed description of a preferred, but not exclusive, embodiment of an apparatus for treating neurological disorders according to the present invention. Such description will be given hereinafter by referring to the enclosed drawings, provided by way of example and not for limitative purposes, wherein:

FIG. 5 shows a functional module adopted in the acquisition module illustrated in FIG. 4b; and FIG. 6 shows a recording of local electric biopotentials, or "local field potentials", from the subthalamic nucleus of a Parkinson's patient.

By referring to the mentioned figures, an apparatus for treating neurological disorders by means of brain stimulation has been designated as a whole with 100.

Figure 1:
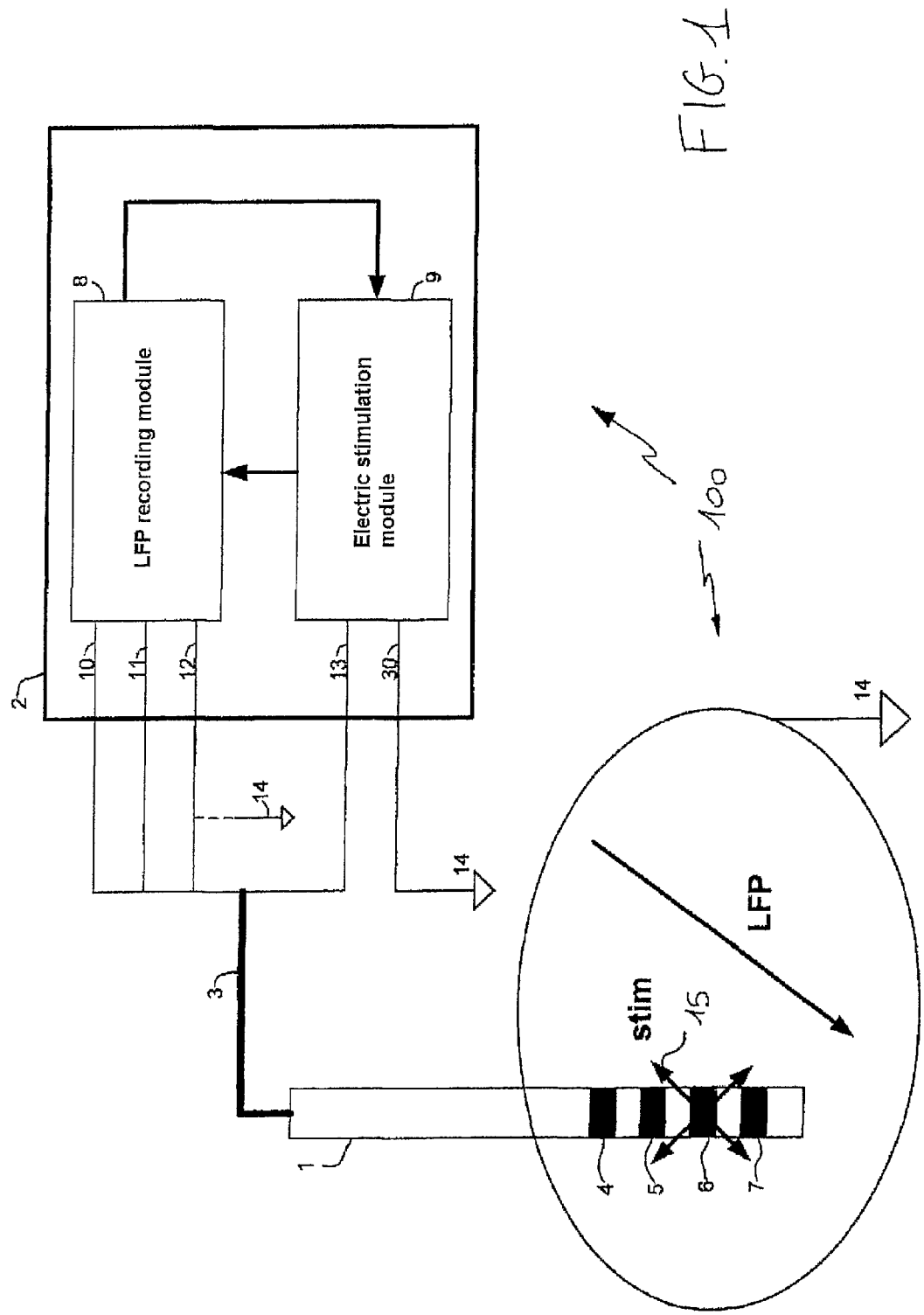
FIG. 1 shows a schematic view of the apparatus for treating the neurological disorders by means of brain stimulation according to the invention.

In particular, the apparatus illustrated in FIG. 1 is suitable for the feedbacked deep brain stimulation able to detect biopotentials from the stimulating electrode or from contiguous electrodes, for correlating such signals to the stimulation effects and for feedbacking the stimulus parameters in order to optimize the therapy onto the patient.

The apparatus described and represented hereinafter has been mainly developed for the chronic treatment (that is with stimulating signals substantially sent continuously) of the Parkinson's disease, although the same apparatus is not to be considered limited to such particular application.

The apparatus 100 first of all comprises at least an electro-catheter 1 implantable in a patient's brain and preferably equipped with at least three contacts. In the preferred configuration the electro-catheter 1 is a depth electrode Medtronic DBS 3387/3389 (Medtronic, Minneapolis, Minn.), with 4 metallic contacts accessible by means of outer connections 4 5, 6, 7, also called electrodes. The same can be implanted in the patient according to what described in the U.S. Pat. No. 5,683,422. As mentioned above, the presence of at least three electrodes or metallic contacts is fundamental which, in the illustrated configuration, are all carried by the same electro-catheter 1; it is obvious that also the use of different electro-catheters, each one equipped with the respective electric contacts/electrodes, could be provided. In its whole structure, the apparatus further comprises an adaptive stimulation system 2 connected to the electro-catheter 1 by means of a multipolar cable 3, as it currently happens in chronic not adaptive stimulation systems. The stimulation system 2 is constituted by two connected and interoperating functional blocks: the module 8 for acquiring a signal characterizing the brain activity coming from the patient's brain and the stimulation module 9 for generating a stimulating signal 15 to be sent to the electro-catheter 1. The electric connections between the electro-catheter and the stimulation system 2 in the here illustrated preferred embodiment are the following:

the contacts 4 and 7 are connected to the inputs 10 and 11 of the acquisition module 8;

the contact 5 is connected to the recording reference 12 of the stimulation module 9 or to an electrode placed at will on the patient 14;

the contact 6 of the electro-catheter is connected to the stimulation electrode 13;

the stimulation reference 30 is connected to an electrode placed at will on the patient 14 or it can be connected to the contact 5, used as recording reference, in this case the stimulation is usually defined bipolar.

Figure 2:
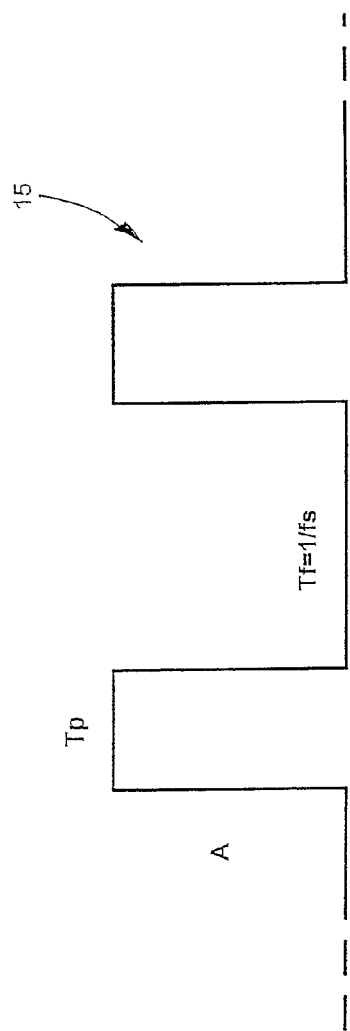
FIG. 2 shows a possible electric stimulus signal sent to a patient's brain.

In the preferred configuration an electrical stimulus signal 15 with monophasic rectangular shape is generated from the stimulation module 9 (FIG. 2). It can be generated by an output high-or-low-impedance electronic circuit, thus generating a respectively current or voltage stimulation. The intensity A of such electric stimulus is initially fixed in advance by the physician, during the control visits. The maximum applicable intensity, such as the stimulating electrode, varies from patient to patient at the physician's discretion who programmes the device during the control visit. Another parameter which can be adjusted initially is the duration of the stimulus Tp and the frequency fs between one stimulus and the subsequent one. The initial stimulation parameters used in the preferred configuration are: 10V or 5 mA with maximum amplitude A, 60 μs for the duration time of the stimulus Tp and 130 Hz as frequency of stimulus fs. The use of other stimulating waveforms such as, for example, continuous-in-time low-frequency waves and DC polarizations of the involved tissues.

Figure 3:
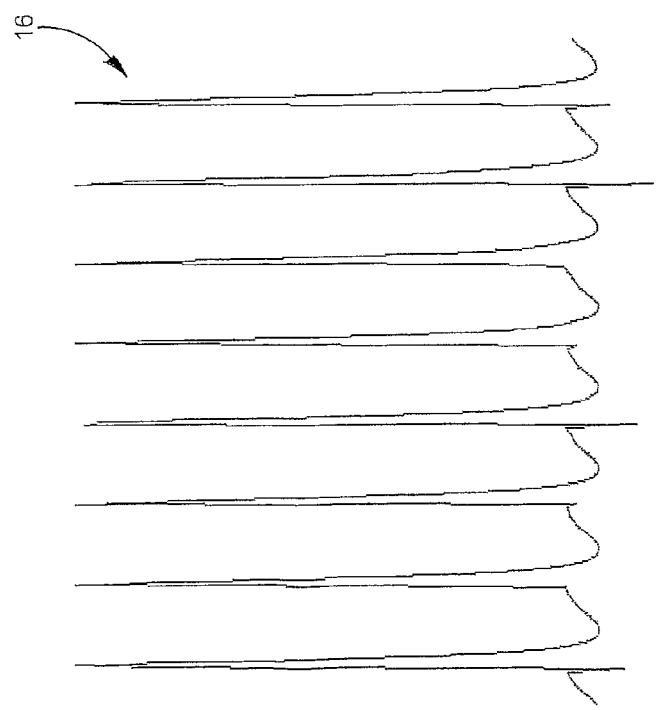
FIG. 3 shows the stimulus artefact received by the apparatus after the initial stimulating signal sending.
Figure 4A:
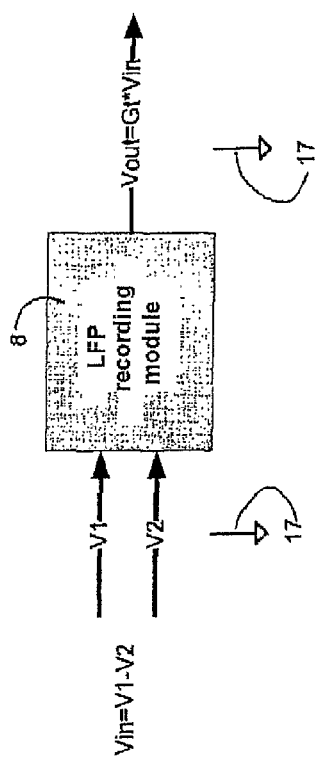
FIGS. 4a and 4b show two block diagrammes of an acquisition module adopted by the apparatus of FIG. 1.
Figure 4B:
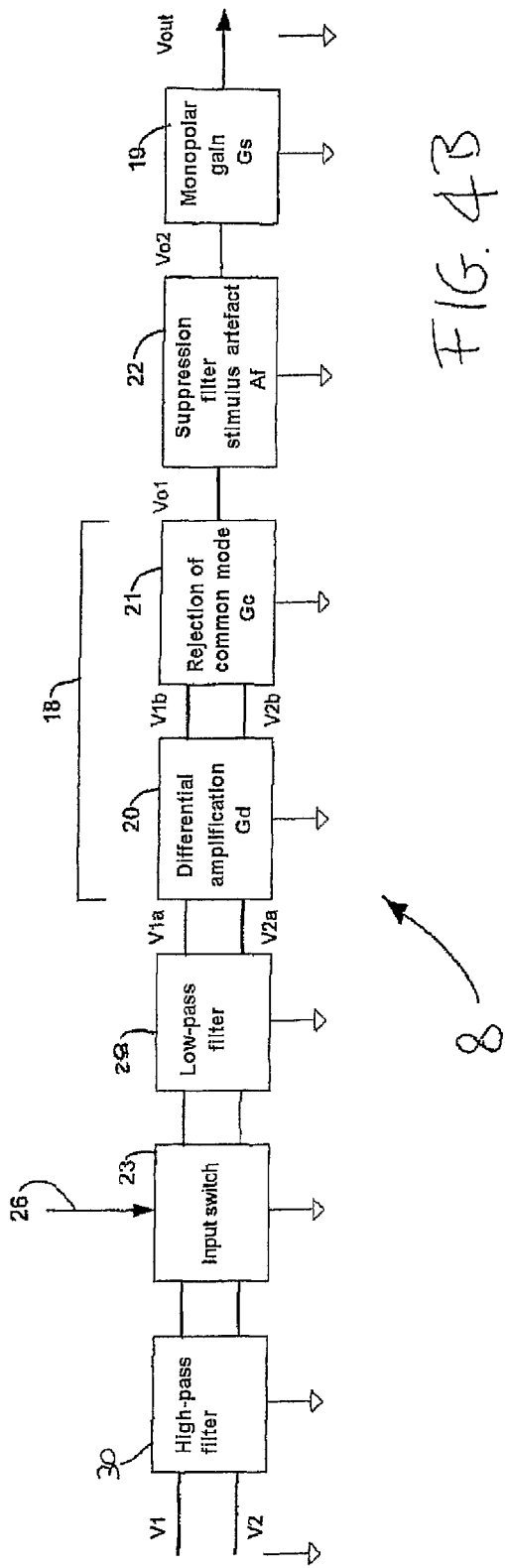

The stimulating signal 15 produces a potential difference between two recording electrodes 4 and 7, such difference is called electric stimulus artefact. The stimulus artefact 16 given by initial stimulating signal in the preferred configuration can be observed in FIG. 3, such signal has been obtained during a control pre-surgical recording. It has to be suppressed from the acquisition module 8 otherwise the local biopotentials cannot be measured. The preferred configuration of the acquisition module 8 of the local biopotentials subject of the present invention is shown in the FIGS. 4A and 4B. The main function of the recording module (FIG. 4A) is that of measuring the electric field variations of the local biopotentials directly correlated to the difference in the electric potentials V1, V2 referred to the common electrode 17 and of amplifying such difference so as to reach a voltage level useful for the analog-to-digital conversion necessary for the signal processing. The total gain of the amplification Gt has to be about in the order of 100 dB, that is for an input differential signal of 10 μV Vin it is necessary to have a voltage Vout of 1V. The acquisition module 8 of the local biopotentials is then composed by two base sub-blocks, the differential amplification block 18 and the monopolar amplification block 19. The differential amplification block 18, in turn, is composed by two modules 20, 21, the first one amplifies the input potential difference, the second one performs the V1b-V2b difference by reducing the signal of common mode. The module 18, then, generates an output voltage Vo1 referred to the common potential 17. For the module 18 the following equations between the involved voltages are defined:

$$V_{1a} = V_{cm} + \frac{V_{in}}{2},$$

$$V_{2a} = V_{cm} - \frac{V_{in}}{2},$$

$$V_{in} = V_{1a} - V_{2a}$$

Wherein Vcm is the voltage of common mode existing on both electrodes, Gd is the differential gain and Gc is the gain of common mode, that is the rejection of common mode. In the ideal case Gc=0. For a real system the minimum Gc, obtainable with the current technologies, is −90 dB.

Furthermore, for a general differential amplification the Common Mode Rejection Ratio is defined as:

$$CMRR = \frac{G_d}{G_c}.$$

The CMRR defines the quality of a recording system for a classic environment of differential measurement wherein the signal of common mode Vcm is generated by outer noises. Greater is the CMRR, greater is the quantity of measured signal, compared to a decrease in the environmental noises existing on the signal Vo1 outgoing from the module. For the biopotential measurements it is fundamental having a high CMRR, for the acquisition of the local biopotentials the accepted CMRR is typically 130 dB. The total gain Gt of the acquisition module 8, by considering a monopolar gain Gs for the monopolar amplification block 19, is equal to the sum of the two gains, the differential one and the monopolar one:

$$G_t = G_d + G_s$$

The requirements of a system for recording the local biopotentials are then 130 dB of CMRR and 100 dB of Gt. In the application of the method subject of the present invention at the input Vin a stimulus artefact 16 is present which in case it is used as reference is in the order of 10 mV. Such artefact intensity has been measured clinically in control post-surgical visits. If such stimulus artefact is amplified with a usual differential amplification Gd of 80 dB (10 mV->100V), it happens that the differential stage saturates, that is the voltages V1b and V2b cannot be reached as they are higher than the operativity range of the electronic instruments, which typically is equal to the value of the power supply voltages (for example 1V). When a saturation in feedbacked amplification stages (typically operational amplifiers) intervenes, it happens that the reset time for the system's correct operation is longer than the real output time from the instruments' operativity limits. Greater is the gain of the stage which is saturated, greater is the reset time thereof. The reset time of a saturation, in a classic instrumentation for recording the biopotentials, induced by the stimulating signal in the preferred embodiment, does not allow to measure any biopotential. On the contrary, if a differential amplification of Gd 40 dB is performed, there will be an output voltage Vo1 of 1V caused by the same stimulus artefact of 10 mV taken as reference. In this case, the signal Vo1 will be equal to the sum of the stimulus artefact of 1V added to the local measured biopotentials, which from 10 µV will pass to 1 mV. In order to eliminate the stimulus artefact the present invention shows a sub-module for analog filtering 22 which serves to attenuate the artefact of a factor Af through an frequency analog conditioning. In the preferred configuration such elimination is performed by means of a low-pass active filter. Alternatively, a notch filter can be used, tuned onto the stimulus' characterizing frequency by extending the band of the local biopotentials' recorded signal to the high frequencies. By using a frequency conditioning it is then possible to attenuate the stimulus artefact existing on Vo1, which in the case taken as example is of 1V, of at least 60 dB, by bringing it to the level of the local biopotentials' signal on Vo2. In case, a low-pass filter of high order can be used to further decrease the stimulus artefact existing on Vo1. The last amplification block 19 performs the pre-mentioned monopolar amplification Gs of 60 dB onto the filtered signal Vo2 so as to obtain a total gain Gt of 100 dB. There is a limiting factor for the analog suppression of the stimulus artefact: it is given by the rejection of common mode Gc which, by using the current technologies with particular constructive precautions, at minimum is equal to −90 dB. This involves the use of a differential amplification with a Gd of at least 40 dB to obtain an acquisition of standard local biopotentials, that is to have available a CMRR equal to 130 dB. This requirement involves two consequences:

the maximum allowable differential stimulation artefact is 10 mV, by using +−1V as reference for the operativity range of the instrumentation;

upon stressing the system with maximum allowable differential artefact, a filter with an Af attenuation of at least 60 dB at the stimulus characterizing frequency must be used, otherwise the monopolar amplification module 19, which has a Gs of 60 dB, is saturated.

Clearly a high-order active filter (Af 60 dB) is expensive both in size terms and as far as the power consumption is concerned. In case of an application of the present invention in an implantable medical device, the energy consumption and the overall dimensions are two fundamental requirements. The invention, then, is equipped with an additional functional module 23 called Input Switch, which utilizes a synchronization signal 26 coming from the stimulation module 9 in order to bring the voltages Va1 and Va2 to a reference electric potential 17 or to leave the two connections disconnected from the recording system during the stimulation. This module in the preferred configuration is implemented by using two mosfets 27 and 28, as schematically illustrated in FIG. 5. The mosfets' gate is guided by the synchronization signal so that when the stimulating signal is brought onto the biological tissue the voltages V1 and V2, existing on the drains, are guided to the respective sources which are connected to the reference potential 17. The use of another system is here not excluded, with the fundamental requirement of having a synchronization with the stimulation module or of using the same electric stimulus in order to be able to disconnect the inputs of the amplification and filtering modules during the stimulus. Moreover, the use of a functional module 23 for opening and closing the front-end does not eliminate the stimulus artefact. In fact, even failing an electric stimulus, if the electrodes' electro-chemical balances are altered, for example by bringing them to the reference potential 17, a noise signal, which can be compared to the electric stimulus itself, is generated. The transitions' transitory must be then filtered so as to eliminate the high frequencies which constitute a great part of the noise generated by such transition. Therefore, a module 29 is required, which eliminates the other frequencies produced by opening and closing the module 23. By means of the module 23 the stimulus artefact can be reduced by succeeding in decreasing the attenuation requested to the analog filtering module, thus allowing the implementation of the invention in sizes compatible with an implantable device. Furthermore, the polarization voltages of the biological tissue metal interface force the use of the module 30 for the high-pass filtering so as to eliminate the voltages of common mode and DC differentials produced by the minimum differences of the interface electro-chemical balances. The block 29 can be arranged, as in the preferred embodiment, at the input of the instrumentation or, at will, inside the acquisition chain. The use of an analog frequency conditioning and of an opening and closing circuit synchronized by the stimulating signal are two fundamental blocks of the invention both for the method and for the device. Clearly they can be used at the same time or singularly with relation to the system implementation type, inner implementation, in an implanted device, or outer implementation, in instrumentation for the intra-surgical targetting of the involved tissue. In case, the illustrated frequency conditioning can be implemented by means of a method involving a moderated analog amplification (Gt 20 dB-40 dB) and a subsequent high-resolution digital conversion which does not exploit the whole dynamics of the converter. In this case the frequency conditioning, that is the use of a low-pass or notch filter to eliminate the stimulus artefact, is performed by means of the signal's digital processing.

These features are not present in the inventions mentioned previously.

Once obtained a Vout signal without stimulus artefact it is processed in the preferred configuration by a Digital Signal Processor. Such signal processing serves to determine the feedback of the stimulation parameters so as to adapt the therapy to the patient's symptomatic state. The use as feedback signal of the electric biopotentials measured by the local tissue around the electrodes—the so-called "local field potentials"—offers a series of operational advantages with respect to the signals of biochemical nature, since the "local field potentials" have specific features which modify instantaneously depending upon the modifications of the patient's clinic conditions (Brown and Williams, 2005). The "local field potentials" reflect the set of the neuronal activity which develops around the electrode therefrom they are recorded and therefore they are particularly sensible to neuronal activities oscillating at population level. Recordings of "local field potentials" carried out in the immediate post-surgical period in parkinsonian and dystonian patients, thereto electrodes for the deep brain stimulation have been implanted, have revealed up to now, in the circuit of the basal ganglia and in particular in the subcircuit including the subthalamus and the globus pallidus, the presence of several oscillatory activities in a quite wide frequency spectrum, from very low frequencies (<10 Hz: Silberstein et al., 2003; Priori et al., 2004) to the beta band (15-35 Hz: Brown et al., 2001; Silberstein et al., 2003; Priori et al., 2004; Kuhn et al., 2005) to oscillations with surprisingly high frequencies (70-80 Hz: Brown et al., 2001; 300 Hz: Foffani et al., 2003). These rhythms constitute quite precise indicators of the system's dopaminergic activity (Brown et al., 2001; Williams et al., 2002; Silberstein et al., 2003; Foffani et al., 2003; Priori et al., 2004) and of the patient's motor condition (Priori et al., 2002; Cassidy et al., 2002; Levy et al., 2002; Foffani et al., 2003; Kuhn et al., 2004;

Foffani et al., 2004; Doyle et al., 2005; Foffani et al., 2005c). In particular, the beta band reflects the bradykinetic/akinetic symptomatology (Brown, 2003), the low frequencies designate the hyperkinetic symptomatology (Silberstein et al., 2003; Foffani et al., 2005b) and the high frequencies represent the circuit's natural rhythms which appear only under conditions of sufficient dopaminergic stimulation and which come in direct resonance with the deep brain stimulation (Brown et al., 2001; Foffani et al., 2003; Brown et al., 2004; Foffani et al., 2005). The "local field potentials", thus, offer specific indicators to monitor even very quick variations of the patient's clinic/motor state. By way of example FIG. 6 shows a recording of local electric biopotentials, or "local field potentials", from the subthalamic nucleus of a parkinsonian patient. The figure shows the course of the "local field potential" signal spectrum in terms of time (x axis). At the beginning of the recording the patient is rigid/akinetic (OFF). The "local field potential" signal has rhythms which can be identified in beta band (~15 Hz) and at low frequencies (<5 Hz) (coloured scale: black=minimum power, clear=maximum power). At time 0 the patient receives one levodopa dose. About 25 minutes after the drug administration, the patient's clinical state changes radically (ON): the rigidity/akinesia decreases and the first diskinesias appear. The "local field potential" reflects this state change with precision, with the decrease in beta oscillations, the increase in low-frequency oscillations and the appearance of a very high-frequency rhythm, around 300 Hz.

In conclusion and in contrast with the alternative adaptive brain stimulation techniques, this invention utilizes as feedback signal a biopotential measured by the tissue which is locally stimulated. The tissue, then, is excited by an electrode in a substantially continuous way (chronic treatment) through a potential difference referred to a common reference electrode. On the contrary, the signal for the feedback is measured differentially by two electrodes adjacent the tissue involved by the stimulation referred to the common reference electrode or to a third electrode placed between the two recording electrodes, then in contact to the stimulation site as well. The recorded local biopotential having a very low intensity is amplified with a particular recording system which removes the disorder generated by the stimulation, so as not to saturate the amplification stage. Such recording system, by opening and closing the recording module and an analog filtering on the local biopotential, allows recording signals in the useful band. In case, the illustrated frequency conditioning can be implemented through the signal's digital processing. The signals, filtered by the stimulus artefact and digitalized, are analysed in order to determine the characterizing parameters which can predict the motor fluctuations. At last, it is to be underlined that the described device can be used also in order to look for anatomically the subthalamic nucleus during the surgical implantation phase. In fact, it is known that the $\alpha$ and $\beta$ rhythms are characteristic of the subthalamic nucleus and they are not found if one records from adjacent nervous structures. Furthermore, recent experimental evidences have shown that these rhythms are particularly sensible to stimulation.

This particular aspect offers the possibility of an additional use of the here present invention.

First of all, the stimulation parameters are fixed at a given value, called test stimulation level, with sufficient intensity so as to cause both a clinic effect and the well-known side effects. With the turned-on stimulation (contact 16—FIG. 1) and by contemporarily recording from the adjacent electrodes (contacts 4, 7—FIG. 1) the depth Z of the stimulation site along the descending axis is varied. With this methodology the depth Z of the stimulation site is then feedbacked in the preferred configuration from the intensity of the recorded $\alpha$ and $\beta$ rhythms.

The present invention offers substantial advantages to the current methodology. In the usually performed implantation clinic procedure exploring electrodes, called microelectrodes, are inserted inside the encephalon, in order to record the electric activity of a reduced group of nervous cells. In order to do this the electrodes have available a sharp recording electrode which thus allows to measure electric fields localized around the same. The presence of this geometry, that is the presence of a tip, involves well-known problems.

The electrical field is detected by cells which are very near to the recording electrode, therefore upon gradually inserting the electrode in the encephalon the cells which have produced the recording are destroyed by the passage of the same. This involves that the recording by micro-electrodes can take place only along the descending route. In the ascending route the electrode notoriously does not measure any cellular activity. On the contrary, it is common practice, when any position is looked for, to precede through progressive approachings. In the specific case, the ideal practice would be the one providing the stimulation electrode descending and ascending along the descending axis by varying the depth z so as to progressively approach the target.

By using electrodes like the ones proposed in the present invention there is not the need of having a sharp electrode since the local biopotentials, electric fields generated by the synchronous activity of a set of cells all belonging for example to the subthalamic nucleus, are recorded. The biological structures generating the signal, then, are not destroyed by the electrode's motion and therefore the position thereof can be varied in both directions.

An additional problem, given by the presence of a sharp electrode, is the risk that it can injure a blood vessel during the descending route. By eliminating the sharp electrode, which has the same mechanical features of a thin needle, the clinic risk is then reduced.

By using the device for the surgical targetting the definitive electro-catheter, or other solution having a chamfered tip apt to reduce to minimum the possibility of causing a haemorrhage during the descending route, can be directly used.

The invention achieves important advantages. The system through the analysis of the local potentials acquired on the stimulation site controls the stimulation parameters. In fact, the electro-catheter is of known type and it is utilized as definitive electrode in the DBS implantation; the same currently already has available four metallic contacts accessible from outside. The four metallic contacts serve for having available a geometric variability on the stimulation site, that is the chronic stimulator is connected to the stimulating electrode which gives greater therapeutic effects. The other three contacts are then available for recording local biopotentials (local field potentials). The method and the related instrumentation connect the information, given by the local biopotentials (or "local field potentials"), to the stimulus parameters which are optimized in real time at the fluctuations of the patient's clinic state typical of the Parkinson disease and of the other neuropsychiatric diseases therefor there is the indication for using DBS. Therefore, the adoption of an apparatus allowing to detect the signal characterizing the brain activity, which in turn determines variations in the stimulation parameters and/or variation in the stimulating electrodes' position would allow to optimize the therapeutic use of the deep brain stimulation methodology.

REFERENCES

Brown P, Oliviero A, Mazzone P, Insola A, Tonali P, Di Lazzaro V. Dopamine dependency of oscillations between subthalamic nucleus and palladium in Parkinson's disease. J Neurosci 2001; 21: 1033-1038.

Brown P. Oscillatory nature of human basal ganglia activity: relationship to the pathophysiology of Parkinson's disease. Mov Disord. 2003; 18: 357-363.

Brown P, Williams D. Basal ganglia local field potential activity: Character and functional significance in the human. Clin. Neurophysiol. 2005.

Cassidy M, Mazzone P, Oliviero A, Insola A, Tonali P, Di Lazzaro V, et al. Movement-related changes in synchronization in the human basal ganglia. Brain 2002; 125: 1235-1246.

Doyle L M, Kuhn A A, Hariz M, Kupsch A, Schneider G H, Brown P. Levodopa-induced modulation of subthalamic beta oscillations during self-paced movements in patients with Parkinson's disease. Eur. J Neurosci 2005; 21: 1403-1412.

Foffani G, Priori A, Egidi M, Rampini P, Tamma F, Caputo E, et al. 300-Hz subthalamic oscillations in Parkinson's disease. Brain 2003; 126: 2153-2163.

Foffani G, Bianchi A M, Priori A, Baselli G. Adaptive autoregressive identification with spectral power decomposition for studying movement-related activity in scalp EEG signals and basal ganglia local field potentials. J Neural Eng 2004; 1: 165-173.

Foffani G, Ardolino G, Rampini P, Tamma F, Caputo E, Egidi M, et al. Physiological recordings from electrodes implanted in the basal ganglia for deep brain stimulation in Parkinson's disease. the relevance of fast subthalamic rhythms. Acta Neurochir. Suppl 2005; 93: 97-99.

Foffani G, Ardolino G, Meda B, Egidi M, Rampini P, Caputo E, et al. Altered subthalamo-pallidal synchronisation in parkinsonian dyskinesias. J Neurol. Neurosurg. Psychiatry 2005b; 76: 426-428.

Foffani G, Bianchi A M, Baselli G, Priori A. Movement-related frequency modulation of beta oscillatory activity in the human subthalamic nucleus. J Physiol 2005c; 568: 699-711.

Fogelson N, Pogosyan A, Kuhn A A, Kupsch A, Van Bruggen G, Speelman H, et al. Reciprocal interactions between oscillatory activities of different frequencies in the subthalamic region of patients with Parkinson's disease. Eur. J Neurosci 2005; 22: 257-266.

Kuhn A A, Williams D, Kupsch A, Limousin P, Hariz M, Schneider G H, et al. Event-related beta desynchronization in human subthalamic nucleus correlates with motor performance. Brain 2004; 127: 735-746.

Kuhn A A, Trottenberg T, Kivi A, Kupsch A, Schneider G H, Brown P. The relationship between local field potential and neuronal discharge in the subthalamic nucleus of patients with Parkinson's disease. Exp. Neurol. 2005; 194: 212-220.

Levy R, Ashby P, Hutchison W D, Lang A E, Lozano A M, Dostrovsky J O. Dependence of subthalamic nucleus oscillations on movement and dopamine in Parkinson's disease. Brain 2002; 125: 1196-1209.

Priori A, Foffani G, Pesenti A, Bianchi A, Chiesa V, Baselli G, et al. Movement-related modulation of neural activity in human basal ganglia and its L-DOPA dependency: recordings from deep brain stimulation electrodes in patients with Parkinson's disease. Neurol. Sci. 2002; 23 Suppl 2: S101-S102.

Priori A, Foffani G, Pesenti A, Tamma F, Bianchi A M, Pellegrini M, et al. Rhythm-specific pharmacological modulation of subthalamic activity in Parkinson's disease. Exp. Neurol. 2004; 189: 369-379.

Silberstein P, Kuhn A A, Kupsch A, Trottenberg T, Krauss J K, Wohrle J C, et al. Patterning of globus pallidus local field potentials differs between Parkinson's disease and dystonia. Brain 2003; 126: 2597-2608.

Williams D, Tijssen M, Van Bruggen G, Bosch A, Insola A, Di Lazzaro V, et al. Dopamine-dependent changes in the functional connectivity between basal ganglia and cerebral cortex in humans. Brain 2002; 125: 1558-1569.

The invention claimed is:

1. Apparatus for chronic treating neurological disorders by means of brain stimulation comprising:
at least an electro-catheter (1) implantable into a patient's brain; and
a stimulation device (2) connected to the electro-catheter and comprising:
at least a stimulation module (9) for generating a substantially continuous stimulating signal (15) to be sent to the electro-catheter (1); and
at least an acquisition module (8) of a signal characterizing the brain activity coming from the patient's brain, said characterizing signal being the local field potential and being used in case for modifying the stimulating signal (15),
wherein the stimulation device (2) is able to detect the local field potential characterizing the brain activity also at the same time of sending the stimulating signal (15) to the patient, wherein the acquisition module (8) comprises at least a suppression filter (22) of a stimulus artefact (16), the suppression filter (22) attenuating the stimulus artefact (16) of a factor $A_F$ through a frequency analog conditioning and characterized in that the acquisition module (8) comprises at least two sub-blocks, one differential amplification sub-block (18) and one monopolar amplification sub-block (19), the differential amplification sub-block (18) allowing amplifying the potential difference of the input signals($V1_A$;$V2_A$) to the same and allowing obtaining also a difference in the signals ($V_{O1}$) reducing a signal of common mode, the suppression filter (22) being placed downwards the differential amplification sub-block (18), said suppression filter (22) receiving as input the difference of signals ($V_{O1}$) the monopolar amplification sub-block (19) receiving as input the signal ($V_{O2}$) outgoing from the suppression filter (22).

2. Apparatus according to claim 1, wherein the stimulation device (2) utilizes the characterizing signal for determining the feedback of parameters of the stimulation signal (15) in order to adapt a therapy to a patient's symptomatic state.

3. Apparatus according to claim 1, characterized in that said suppression filter (22) is a low-pass active filter or a notch filter.

4. Apparatus according to claim 1, wherein the stimulation device (2) utilizes the characterizing signal for determining an optimum positioning of the electro-catheter (1) in the subthalamic nucleus during the surgical implantation phase.

5. Apparatus according to claim 1, wherein the electro-catheter (1) is equipped with at least three contacts, at least two contacts (4, 7) acting as sensors and sending the signals received from the patient's brain to the acquisition module (8), at least one contact (6) receiving the stimulating signal (15) from the stimulation module (9).

6. Apparatus according to claim 5, wherein the stimulus artefact (16) is given by the potential difference recorded between the two contacts-sensors (4, 7) and produced by the stimulating signal (15).

7. Apparatus according to claim 1, wherein the acquisition module (8) further comprises a functional module (23) receiving as input a synchronization signal (26) coming from the stimulation module (9), the functional module (23) being placed upwards the differential amplification sub-block (18).

8. Apparatus according to claim 7, wherein the functional module (23) brings the output voltages ($V_{1A}$; $V_{2A}$) to reference electric potential (17) during the sending of the stimulation signal (15) or wherein the functional module (23) decouples the output voltages ($V_{1A}$; $V_{2A}$) from the input voltages (V1;V2) during the sending of the stimulation signal (15).

9. Apparatus according to claim 8, wherein the acquisition module (8) further comprises a module (29) for eliminating the high frequencies produced by the operation of the functional module (23), said module (29) being a low-pass filter placed operatively downwards the functional module (23).

10. Apparatus according to claim 1, wherein the acquisition module (8) further comprises a module (30) for the high-pass filtering apt to eliminate the voltages of common mode and differentials produced by the differences in the interface electro-chemical balances.

11. Apparatus according to claim 1, wherein a frequency conditioning is implemented by means of a reduced analog amplification and a subsequent high-resolution digital conversion.

* * * * *